(12) United States Patent
Baltayan

(10) Patent No.: US 10,492,972 B2
(45) Date of Patent: Dec. 3, 2019

(54) ARTICULATING CHIN REST ASSEMBLY

(71) Applicant: Serge Varoujan Baltayan, Los Angeles, CA (US)

(72) Inventor: Serge Varoujan Baltayan, Los Angeles, CA (US)

( * ) Notice: Subject to any disclaimer, the term of this patent is extended or adjusted under 35 U.S.C. 154(b) by 300 days.

(21) Appl. No.: 14/918,860

(22) Filed: Oct. 21, 2015

(65) Prior Publication Data

US 2017/0112700 A1    Apr. 27, 2017

(51) Int. Cl.
| A61G 13/12 | (2006.01) |
| A61F 5/37 | (2006.01) |
| A61G 13/10 | (2006.01) |

(52) U.S. Cl.
CPC ........ *A61G 13/1215* (2013.01); *A61F 5/3707* (2013.01); *A61G 13/101* (2013.01)

(58) Field of Classification Search
CPC .............. A61G 13/1215; A61G 13/101; A61G 13/126; A61G 13/128; A61G 13/1295; A61F 5/3707
See application file for complete search history.

(56) References Cited

U.S. PATENT DOCUMENTS

| 2,452,816 | A | * | 11/1948 | Wagner | .................. | A61G 13/12 5/636 |
| 3,188,079 | A | * | 6/1965 | Boetcker | ................ | A61G 13/12 297/391 |
| 5,494,048 | A | * | 2/1996 | Carden | .................. | A61F 5/3707 128/876 |
| 7,055,524 | B1 | * | 6/2006 | Taimoorazy | .......... | A61F 5/3707 128/845 |
| 7,096,869 | B1 | * | 8/2006 | Orlewicz | .............. | A61F 5/3707 128/845 |
| 8,656,536 | B1 | * | 2/2014 | Sorg | .................... | A61G 13/1205 378/209 |
| 2005/0160532 | A1 | * | 7/2005 | Froelich | .................. | A61G 13/12 5/637 |
| 2005/0247309 | A1 | * | 11/2005 | Reddick | ................ | A61F 5/3707 128/200.26 |
| 2008/0041374 | A1 | * | 2/2008 | Reddick | .................. | A61G 13/12 128/200.26 |
| 2010/0018537 | A1 | * | 1/2010 | Soto | ........................ | A61G 13/12 128/845 |
| 2010/0307509 | A1 | * | 12/2010 | King | .................. | A61G 13/1215 128/845 |

(Continued)

*Primary Examiner* — Kristen Matter
(74) *Attorney, Agent, or Firm* — Omni Legal Group, PLL; Omid E. Khalifeh

(57) ABSTRACT

An articulated chin rest is assembly is provided for supporting the chin of a patient under monitored anesthesia care, sedation, general anesthesia, or other medical procedure to ensure that their airway is unobscured. The assembly may comprise a clamp adaptable to grip a variety of structures, a first and a second length of rigid material sequentially and rotatably connected to the clamp, and a chin rest finally rotatably connected to the second length of rigid material. Means for rotatably linking the clamp, first and second lengths of rigid material, and chin rest allow each element to rotate in three dimensional space so that the assembly mechanically mimics, and is ultimately usable in place of, an anesthesiologist's hand for tilting the patient's head and securely supporting the patient's chin.

5 Claims, 6 Drawing Sheets

(56) References Cited

U.S. PATENT DOCUMENTS

2011/0036355 A1\* 2/2011 Farnum .............. A61G 13/1215
128/845
2012/0260429 A1\* 10/2012 Rolfes .................. A61G 13/101
5/637

\* cited by examiner

ARTICULATING CHIN REST ASSEMBLY

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material that is subject to copyright protection. This patent document may show and/or describe matter that is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to devices used during medical procedures and, more particularly, to an apparatus for externally maintaining an open airway in a patient during treatment and even procedures involving monitored anesthesia care.

BACKGROUND

Airway obstruction is a problem that commonly occurs during medical procedures in which a patient is placed under sedation, general anesthesia, or monitored anesthesia care (MAC). In many such cases, patients are placed into an unconscious state without any intubation or other invasive breathing apparatus in their airway. Because of this, relaxed tongue and other airway tissues commonly sag and cause the patient's airway to become compromised. In particular, it is commonly known that obstruction of the airway may cause the patient's oxygen levels to drop to unsafe levels.

One method of opening a patient's airway has been for an anesthesiologist to physically lift the patient's chin and move the patient's jaw until monitors indicate that the patient is receiving enough oxygen, or in other words, that the patient's blood is experiencing optimal oxygen saturation. Once a position providing the patient with optimal oxygen saturation is achieved, the anesthesiologist must continue to hold his jaw in this position, or another more suitable position, until the patient regains consciousness. In some instances, anesthesiologists must resort to using additional tools, such as towels to help prop the patient's head in an optimal position. However, anesthesiologists may have many other responsibilities during a procedure. For instance, they are often responsible for managing and treating changes in heart rate and blood pressure in addition to breathing as such changes occur. Thus, personally maintaining the patient's jaw, chin, and head in a position that allows optimal oxygen saturation can be distracting and inefficient for anesthesiologists and other personnel involved in the treatment of the patient.

Some devices have been proposed to solve this problem. For example, U.S. Pat. No. 6,969,366 to Reddick discloses a chin support device having a malleable shaft placed between patient's chin and chest. This device is deficient, however, because it is only capable of providing hands-free support of the patient's chin while the patient is unconscious along his back. The device is not applicable, then, for procedures which may require the patient to lie along his side or stomach. Additionally, the proposal is deficient because it obscures a patient's neck and chest. This makes the device wholly unusable for procedures that require ready, unobscured access to the patient's neck or chest.

As another example, U.S. Pat. No. 7,096,869 to Orlewicz discloses a table top neck support which is placed beneath the patient's head. A swing arm having an orthogonal bend extends from the neck support to support the patient's chin. This proposal is deficient, however, because it is cumbersome and is also limited to procedures wherein a patient is lying along his back.

As yet another example, U.S. Pat. No. 6,171,314 to Rotramel discloses a device having a chin support along with supportive members that flank the chin support. As with prior examples, this proposal is deficient because the patient must be in a supine position, and also because the flanking members obscure portions of the patient's neck, face, and jaw which an anesthesiologist or other medical professional may have need to readily access during the procedure.

Although various proposals have been made to solve the problem, none of those in existence combine the characteristics of the present invention. Therefore, there is a need for a non-invasive device which provides hands-free and adjustable support to a patient's chin and/or jaw to allow anesthesiologists and other medical personnel to more efficiently monitor and provide care to the patient.

SUMMARY

The present disclosure is directed to a low-profile assembly comprising an arm capable of articulation in three dimensions to provide adjustable chin support for maintaining an open airway in a patient under sedation, general anesthesia, monitored anesthesia care (MAC), or other medical procedure.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In an embodiment, the articulating chin rest assembly comprises an arm having at least a first length and a second length of rigid material, sequentially aligned and rotatably connected to one another. A clamp may be rotatably connected to a proximate end of the first length, and a chin rest is rotatably connected to a distal end of the second length. More particularly, the rotatable connection of at least the first length and clamp as well as the second length and chin rest may be configured to allow articulation of the assembly in three dimensions. For instance, a means for rotatably connecting the first length and the clamp may be a ball joint permitting the first length to articulate in three dimensions with respect to the clamp. Similarly, a means for connecting the second length and chin rest may be a ball joint permitting the chin rest to articulate in three dimensions with respect to the second length.

Finally, the first and second lengths of rigid materials may be rotatably connected to one another by what is known in the art of articulating arms as a center lock. In some embodiments, providing a center lock may ensure that each of the joints simultaneously freezes the desired articulation of the assembly so that it remains in a fixed position, supporting the patient's chin in a desired manner, until an anesthesiologist, surgeon, or other medical professional chooses to adjust the position of the assembly.

It is contemplated that, in practice, using the chin rest assembly to support a patient's chin to maintain an open airway frees the medical professional's hands and attention so that he or she may focus on other, potentially life saving, responsibilities regarding the patient's care.

It is further contemplated that permitting three dimensional articulation among multiple joints may allow anesthesiologists and other medical professionals to easily adjust the chin rest assembly so that it can support any unique patient's chin at virtually any angle that may provide the patient with optimal air flow and oxygen saturation. Indeed, the adjustability of the chin rest assembly even mechanically mimics the ability of a medical professional to adjust his own arm, wrist and hand in individually tilting a patient's chin, jaw, and head to provide an open airway. Such versatility permits an anesthesiologist or medical professional to provide an open air-way in a hands-free manner when a patient is lying on his side, stomach or back because the chin rest assembly may stretch, rotate, and/or fold at one or more different joints, with each joint moving independent of each other joint. Indeed, using the articulating chin rest assembly, an anesthesiologist or medical professional can remove their hands from the field of treatment to make themselves available to perform other duties, such as provide medication, make notes in the patient's chart, and attend to the various monitors provided for the operation, among others.

The articulating chin rest assembly may not only be rotatably adjusted in three dimensions to embody various jointed shapes, but also be mounted, via the clamp, on innumerable structures. In some embodiments, for example, the clamp comprises an upper and a lower jaw configured to securably grip a variety of structures, further supporting its versatility in treating various patient's experiencing various procedures and treatments. For example, many clamps are known to have jaws which are adjustable along a shaft. Using a tension bar, or even a screw, the upper and lower jaws may be adjustable along the shaft in order to receive and securably grip structures of various widths. Additionally, a portion of either the upper or the lower jaw, or both, may comprise a piece which, when removed, reveals a void defined by the upper or lower jaw configured to securely receive round or irregularly shaped structures. Thus, the clamp may securably grip a flat surface such as a table top, a stretcher, or an operating room tray or operating room table. The clamp may also securably grip a round structure such as a post, pole, or rail, such as those commonly featured on gurneys and hospital beds. Of course, one skilled in the art will recognize that the clamp may be configured to secure the arm to innumerable structures; the foregoing are offered by way of example only and not of limitation.

In an embodiment, the chin rest may also be configured to enhance medical versatility of the articulating chin rest assembly. For example, the chin rest may comprise a cushioned, elongated cylinder configured to fit supportively beneath a patient's chin. This type of configuration may be universally applicable to any patient. In another embodiment, however, the chin rest may comprise an elongated cylinder that is flexible to permit bending so that it conforms to the shape of a patient's lower mandible. In still another embodiment, the chin rest may comprise a rigid or flexible tray. The rigid or flexible tray may be formed to the shape of a lower mandible. Thus, it is to be understood that the chin rests are interchangeable with other chin rests of various shapes and sizes, as desired by or available to the anesthesiologist or other medical professional.

Additional aspects of the articulating chin rest assembly are contemplated, of course. For example, the first and second lengths of rigid material may be telescoping tubes. This may allow anesthesiologists and medical professionals to adjust the total length in addition to the ultimate shape of the assembly. The rigid material itself may comprise metal tubing, or PVC, or any other material sufficient to maintain a patient's head in a particularly selected position by providing support to his chin. Of course, such materials are offered by way of example only and not of limitation. Various shapes, lengths, and materials comprising the arm are contemplated. It is contemplated, for example, that the first and second lengths of rigid material comprising the arm of the assembly may be thin tubes having a low-profile, which ensures that any obstruction of the field of treatment or operation is avoided.

Thus, it is an object of the invention to provide hands-free support for a patient's chin to maintain the patient's head in a position that permits an open airway while the patient is under monitored anesthesia care, sedation, general anesthesia, or other medical procedure.

It is another object of the invention to provide hands-free support to open or maintain a patient's airway while the patient is in any of a supine, prone, side, inclined, or any other position.

It is yet another object of the invention to avoid obstructing areas of a patient's head, neck, jaw, and chin so that oral, maxillofacial and other head and neck surgeries may be performed while the device is in use.

One or more of the above-disclosed embodiments, in addition to certain alternatives, are provided in further detail below with reference to the attached figures. The disclosed subject matter is not, however, limited to any particular embodiment disclosed.

Figure 1:
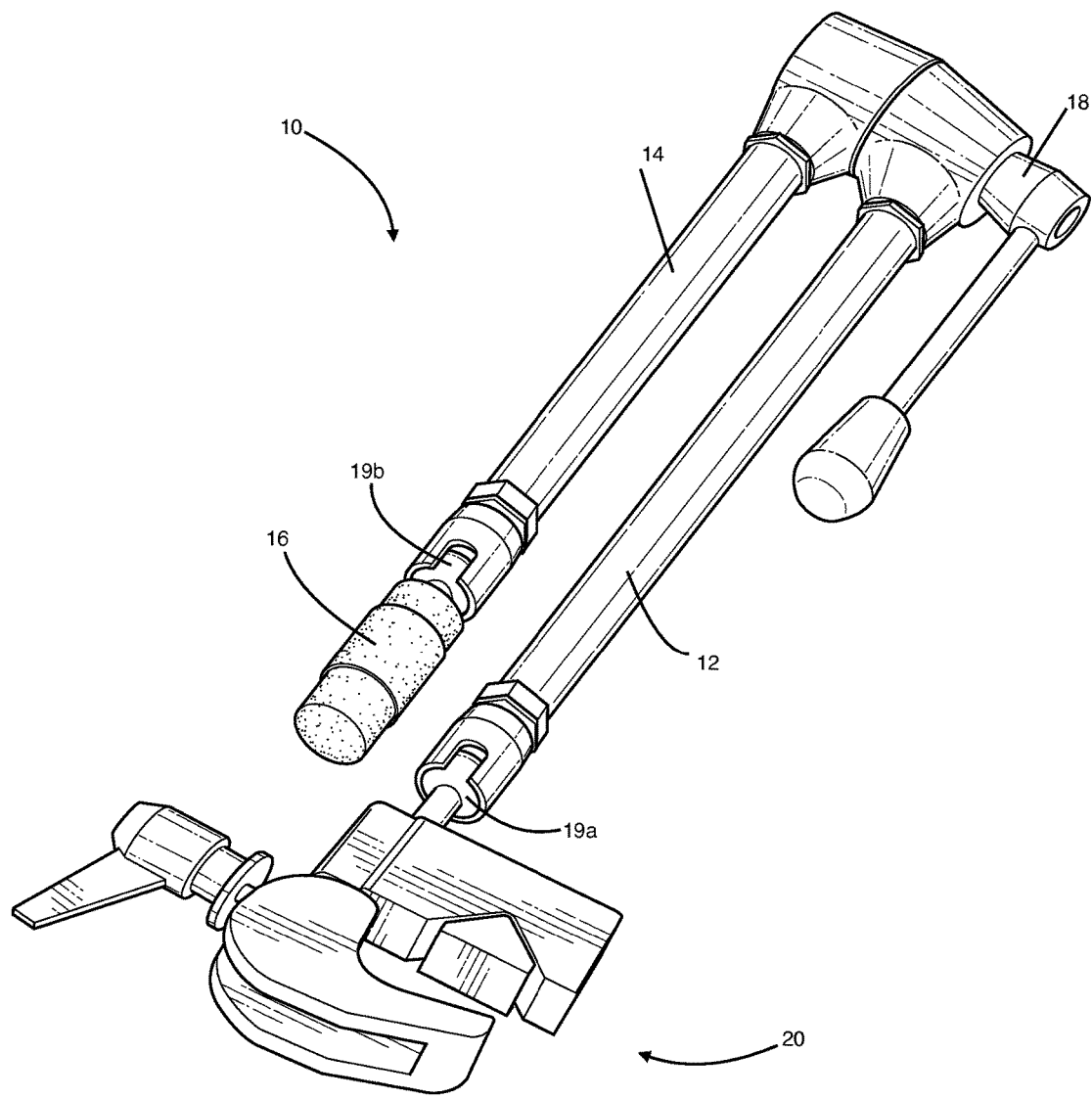
FIG. 1 is a perspective view of an articulated chin rest according to one embodiment of the invention.

The disclosed embodiments may be better understood by referring to the figures in the attached drawings, as provided below. The attached figures are provided as non-limiting examples for providing an enabling description of the apparatus claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

Figure 2:
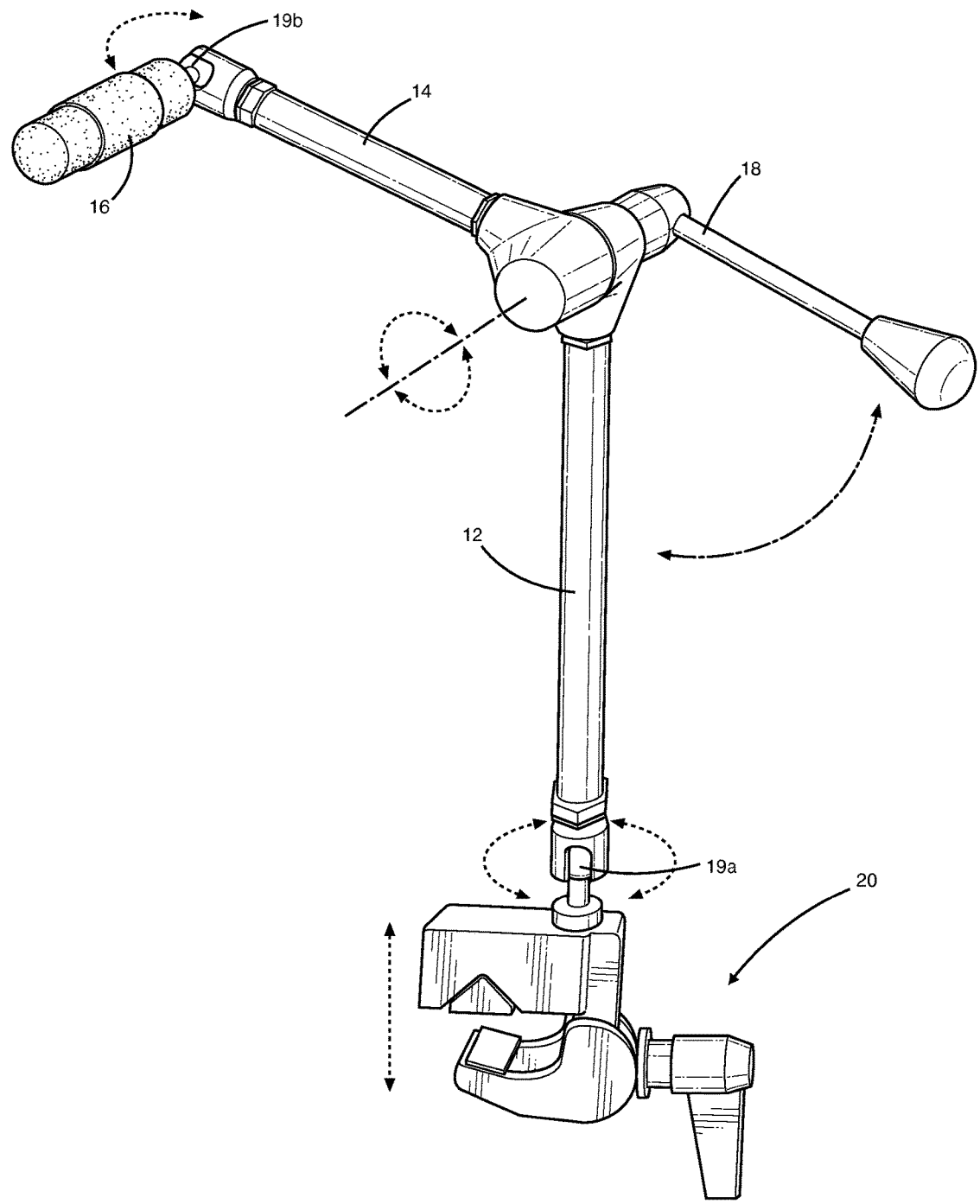
FIG. 2 is an alternative perspective view of an articulated chin rest according to one embodiment of the invention.

With reference to FIGS. 1 and 2, the articulating chin rest assembly 10 comprises an arm having a first length 12 of rigid material and a second length 14 of rigid material. The first and second lengths 12, 14 of rigid materials may be rotatably connected to one another by what is known in the art of articulating arms as a center lock 18. A clamp 20 may be rotatably connected 19a to a proximate end of the first length 12, and a chin rest may be rotatably connected 19b to a distal end of the second length 14. More particularly, the rotatable connection 19a of the first length 12 and clamp 20 as well as the rotatable connection 19b of the second length 14 and chin rest 16 may be configured to allow articulation of the assembly in three dimensions. For instance, a means for rotatably connecting 19a the first length 12 and the clamp 20 may be a ball joint permitting the first length 12 to articulate in three dimensions with respect to the clamp 20. Similarly, a means for rotatably connecting 19b the second length 14 and chin rest 16 may be a ball joint permitting the chin rest to articulate in three dimensions with respect to the second length.

In some embodiments the center lock 18 may be operable to simultaneously lock all of the joints in a desired articulation of the assembly 10 so that the assembly 10 remains in a fixed position, supporting the patient's chin in a desired manner, until an anesthesiologist, surgeon, or other medical professional chooses to adjust the position of the assembly 10.

Each of the first and second lengths 12, 14 of rigid material may be up to about 12 inches long, so that when fully extended, the articulating chin rest assembly 10 extends to more than about 24 inches, or 2 feet, long. The first and second lengths 12, 14 may be longer or shorter as desired, and may even be differently sized from one another. Indeed, in one embodiment at least one of the first and second lengths 12, 14 is a telescoping tube.

Figure 3:
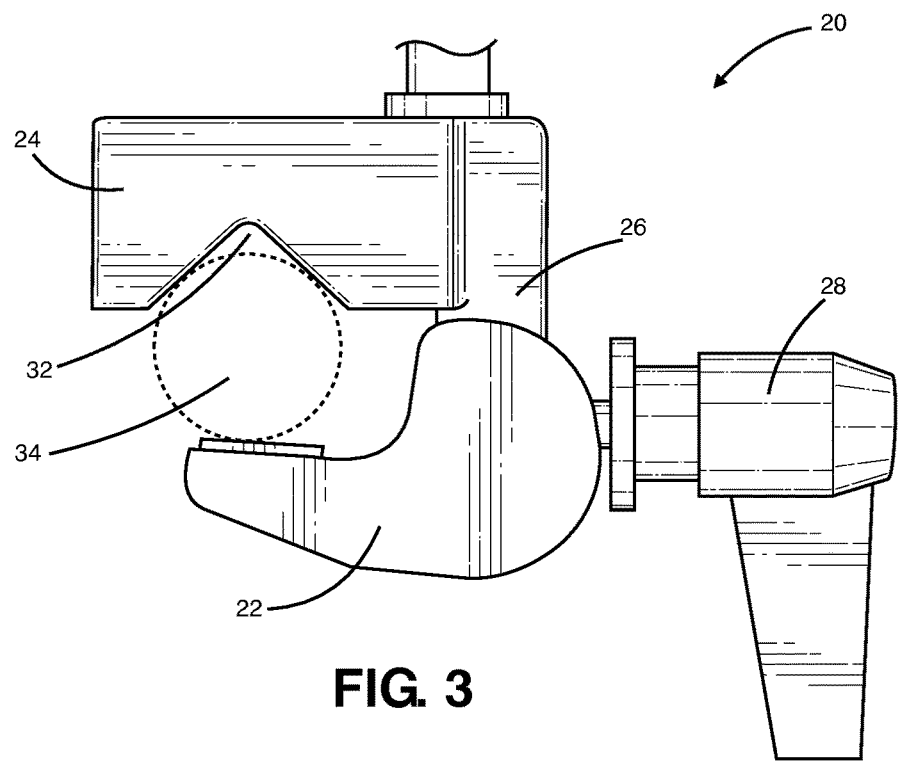
FIG. 3 is a close-up plan view of a jaw portion of the articulated chin rest according to one embodiment of the invention.
Figure 4:
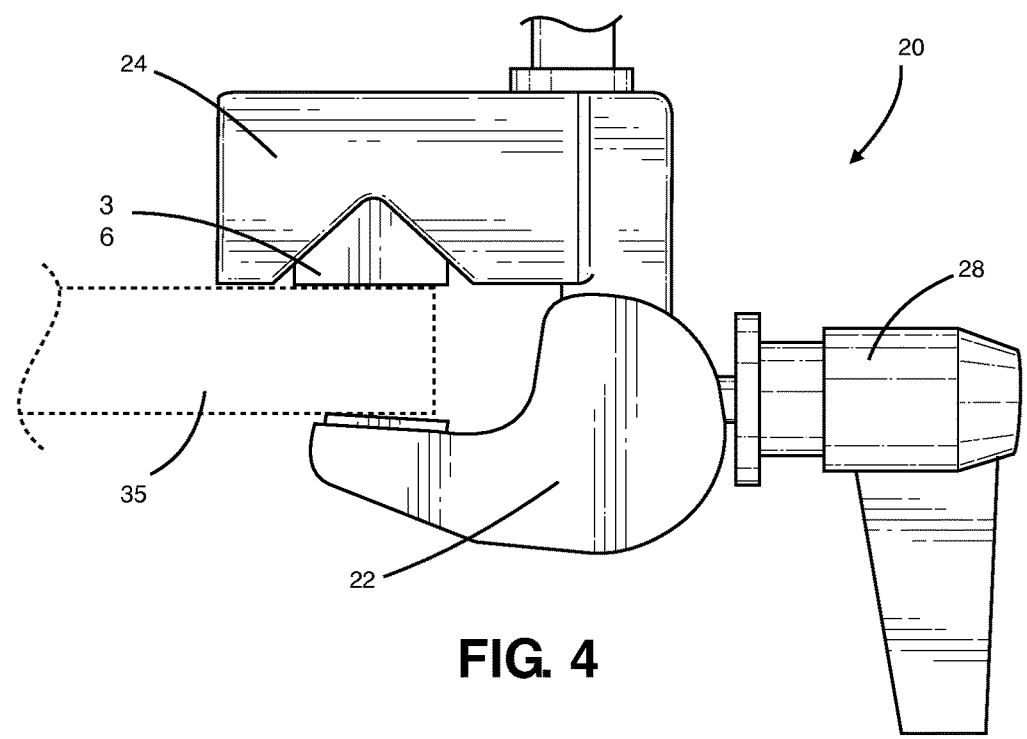
FIG. 4 is a close-up plan view of a jaw portion of the articulated chin rest according to an alternative embodiment of the invention.

With reference to FIGS. 3 and 4, the clamp may comprise a lower jaw 22 and an upper jaw 24 configured to securably grip a variety of structures. For example, many clamps are known to have jaws which are adjustable along a shaft 26. In some embodiments, the clamp 20 further comprises a tension bar 28 to permit an attending medical professional to adjust the distance between the upper and lower jaws 22, 24 along the shaft 26 in order to receive structures of various widths. For example, the distance between the jaws may vary from about 0.25 inches to about 3 inches. As such, it is contemplated that the distance between the upper and lower jaws 22, 24 may be adjusted to grip structures that vary in thickness such as those chosen from a thin tray to a thick as a bedframe or even table top.

Additionally, a portion of either the upper or the lower jaw 22, 24, or both, may comprise a piece 36 which, when removed, reveals a void 32 configured to securely receive round 34 or irregularly shaped structures. As may be seen from the figure, providing a jaw portion which defines a shaped void 32 provides additional surface area with which to grip the supportive structure 34. Thus, the clamp may securably grip a flat structure 35 such as a table top, a stretcher, or an operating room tray, table, or even bracket. The clamp 20 may also securably grip a round structure 34 such as a pole or rail, known to be provided alongside gurneys and hospital beds. Of course, one skilled in the art will recognize that the clamp 20 may be configured to secure the assembly 10 to innumerable structures; the foregoing are offered by way of example only and not of limitation.

Figure 5:
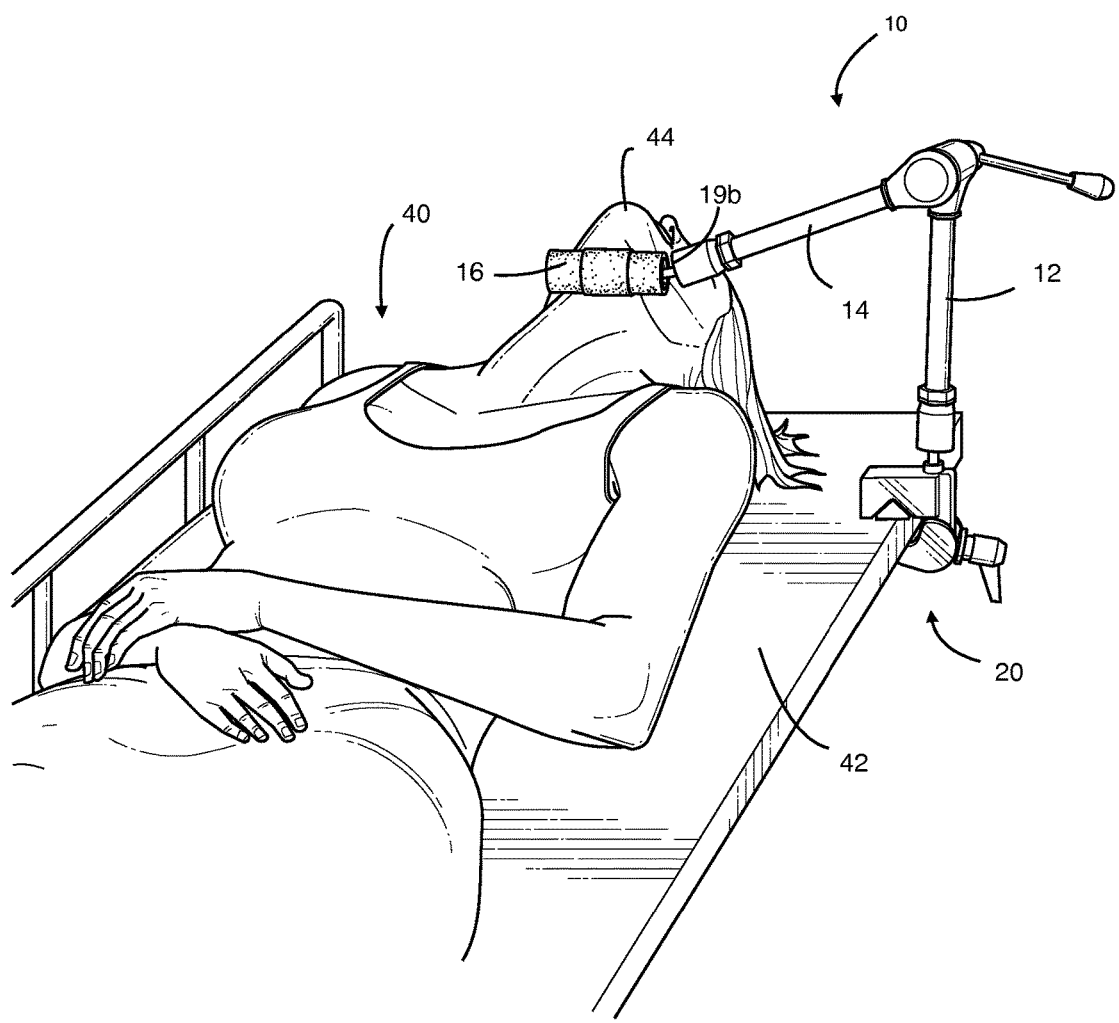
FIG. 5 shows an embodiment of the articulated chin rest in use to maintain a patient's head at a particular orientation.
Figure 6:
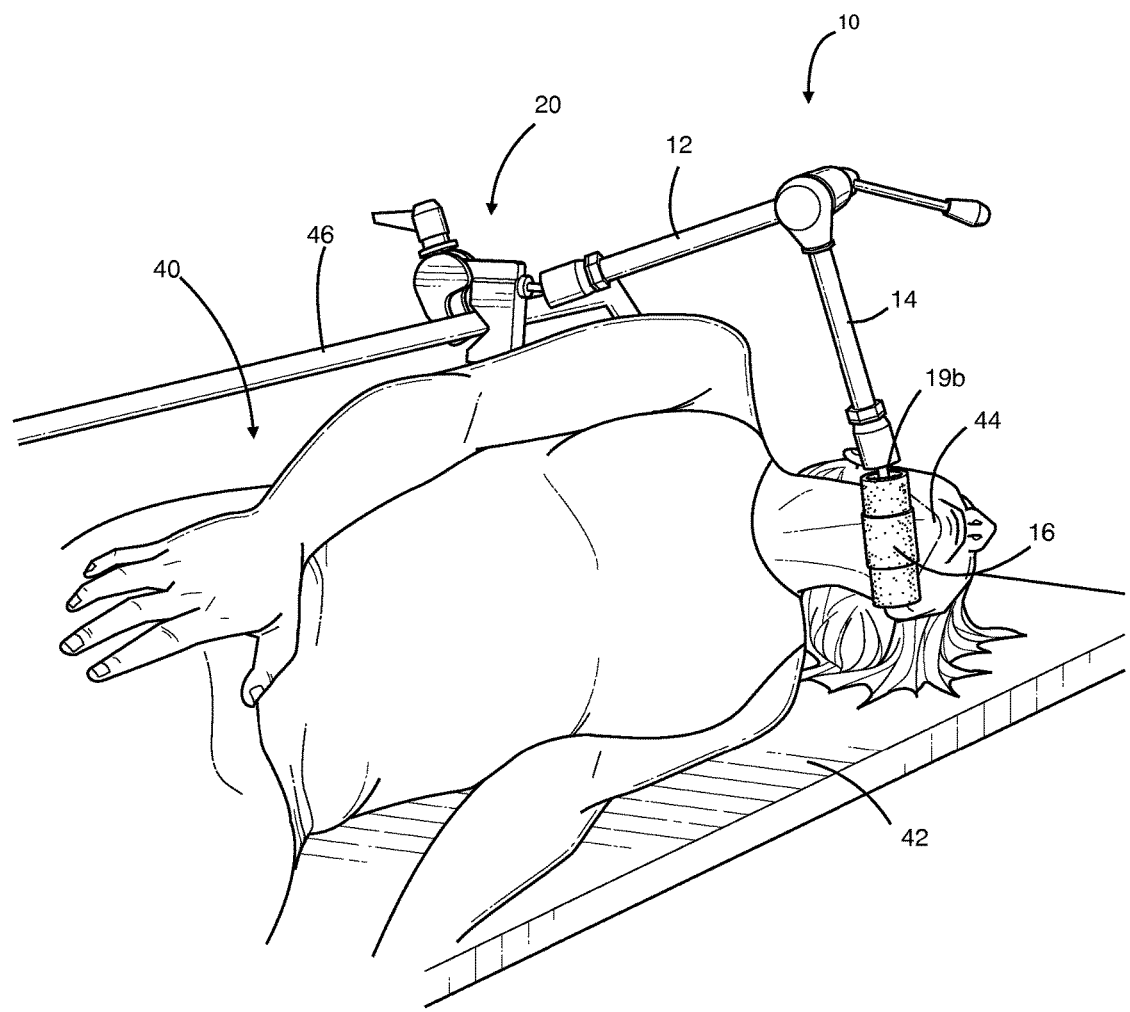
FIG. 6 shows an embodiment of the articulated chin rest in use to maintain a patient's head at an alternative orientation.

FIGS. 5 and 6 provide illustrations of an embodiment of the assembly in use. For instance, with reference to FIG. 5, a patient 40 is shown laying along her back, or in a supine position, along a flat surface 42. The clamp 20 is positioned to grip the surface 42 and the first and second lengths 12, 14 of rigid material are bent so that the chin rest 16 reaches just below the patient's 40 chin 44. It should be noted that the chin rest 16 is also bent with respect to the second length 14 of rigid material at its rotatable connection 19b. Thus the patient's chin 44 is sturdily maintained in a tilted position so that her airway may be unobstructed. It should also be noted that the low profile of the assembly 10 avoids obscuring portions of the patient's body to which an anesthesiologist or other medical professional may need access. At the same time, because the anesthesiologist's hands are freed from personally supporting the patient's 40 chin 44 while using the assembly, the anesthesiologist, or other medical professionals as the case may be, may be free to take care of other matters relating to the care of the patient until it becomes desirable to adjust or remove the assembly.

With reference to FIG. 6, the patient 40 is shown laying along her side on the surface 42. Here, the assembly 10 is mounted to a rail 46 running along the surface 42. Having mounted the assembly 10 in this manner, it may be seen that the first and second lengths 12, 14 of rigid material are bent so that the chin rest 16 reaches just below the patient's 40 chin 44. It should be noted that the chin rest 16 is also bent with respect to the second length 14 of rigid material at its rotatable connection 19b. As in FIG. 5, the patient's chin 44 is sturdily maintained in a tilted position so that her airway may be unobstructed, and the low profile of the assembly 10 avoids obscuring portions of the patient's body to which an anesthesiologist or other medical professional may need access.

One skilled in the art will recognize that the assembly is not limited to use with a particular type of flat bed, table, or rail. Indeed, it well known that patient's may be found on various surfaces, and depending on the procedure, in various positions. Although shown lying on her back and on her side respectively, the patient 40 may also be treated while laying on her stomach, while inclined in a semi seated position, or any other position.

Figure 7A:
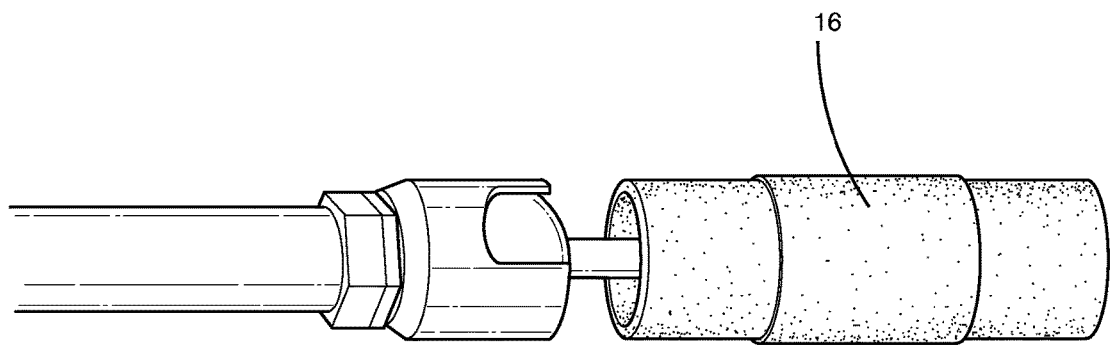
FIG. 7A shows a close-up perspective view of an embodiment of the chin rest portion of the articulated chin rest.
Figure 7B:
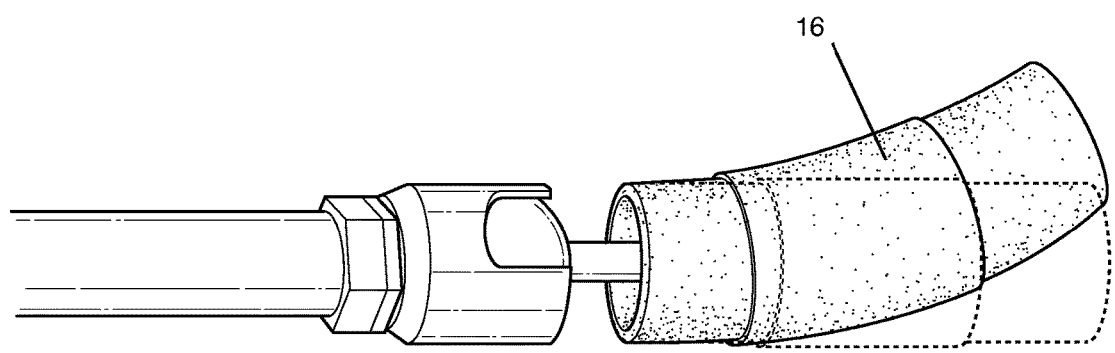
FIG. 7B shows a close-up perspective view of an alternative embodiment of the chin rest portion of the articulated chin rest.

In an embodiment, the chin rest may also be configured to enhance medical versatility of the articulating chin rest assembly. For example, the chin rest 16 may comprise a cushioned, elongated cylinder, as shown in FIG. 7A, configured to fit supportively beneath a patient's chin. This type of configuration may be universally applicable to any patient. In another embodiment, however, the chin rest 16 may comprise an elongated cylinder that is flexible to permit bending, as in FIG. 7B, so that it conforms to the shape of a patient's lower mandible. In still another embodiment, the chin rest may comprise a rigid or flexible tray. The rigid or flexible tray may formed to the shape of a lower mandible. Thus, it is to be understood that the chin rests are interchangeable with other chin rests of various shapes and sizes, as desired by or available to the anesthesiologist or other medical professional.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, the particular shape of the first and second lengths of rigid material may take various shapes. They may, in some embodiments, be cylindrical, triangular, or even rectangular tubes. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the articulating chin rest assembly with which that terminology is associated. In general, the terms used in the following claims should not be constructed to limit the articulated chin rest to the specific embodiments disclosed in the specification unless the above description section explicitly define such terms. Accordingly, the actual scope encompasses not only the disclosed embodiments, but also all equivalent ways of practicing or implementing the disclosed apparatus. The above description of embodiments of the articulating chin rest assembly is not intended to be exhaustive or limited to the precise form disclosed above or to a particular field of usage.

While specific embodiments of, and examples for, the apparatus are described above for illustrative purposes, various equivalent modifications are possible for which those skilled in the relevant art will recognize.

While certain aspects of the apparatus disclosed are presented below in particular claim forms, various aspects of the apparatus are contemplated in any number of claim forms. Thus, the inventor reserves the right to add additional claims after filing the application to pursue such additional claim forms for other aspects of the articulating chin rest.

What is claimed is:

1. An articulating chin rest assembly for externally preventing airway obstruction in a patient, comprising:
   an adjustable clamp;
   an articulating arm having at least a first length of rigid material extending from the clamp and a second length of rigid material extending from the clamp;
   a chin rest having a first chin rest end and a second chin rest end, wherein the first chin rest end extends from the second length, and the chin rest comprises a cushioned, elongated cylinder having
   a) an inner cylinder portion having a first diameter;
   b) a center cylinder portion having a second diameter; and
   c) an outer cylinder portion having a third diameter;
   wherein the second diameter of the center cylinder portion is larger than the first diameter of the inner cylinder portion, wherein the second diameter of the center cylinder portion is larger than the third diameter of the outer cylinder portion, and wherein the elongated cylinder is configured to fit supportively beneath a patient's chin;
   means for rotatably connecting the clamp to an end of the first length, means for rotatably connecting another end of the first length to an end of the second length, and means for rotatably connecting another end of the second length to the chin rest; and
   a means for simultaneously locking each of the clamp, first and second lengths and chin rest in a chosen position.

2. The assembly of claim 1, wherein the elongated cylinder is malleable to permit the bending of the cylinder to conform to the shape of a patient's lower mandible.

3. The assembly of claim 1, wherein the means for rotatably connecting the clamp to the first length, and means for rotatably connecting the second length to the chin rest is a ball joint.

4. The assembly of claim 1, wherein the means for simultaneously locking each of the clamp, first and second lengths and chin rest in a chosen position comprises a locking lever and further defines the means for rotatably connecting the first and second lengths of rigid material.

5. The assembly of claim 1, wherein each of the first and second lengths of rigid material are telescoping tubes.

* * * * *